(12) United States Patent
Mori et al.

(10) Patent No.: US 7,300,675 B2
(45) Date of Patent: Nov. 27, 2007

(54) LIPOLYSIS STIMULATOR

(75) Inventors: Shinobu Mori, Tochigi (JP); Hiroshi Kusuoku, Tochigi (JP); Mayumi Sato, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/900,102

(22) Filed: Jul. 28, 2004

(65) Prior Publication Data

US 2005/0064049 A1     Mar. 24, 2005

(30) Foreign Application Priority Data

Jul. 29, 2003  (JP) .............................. 2003-203095
May 26, 2004  (JP) .............................. 2004-156535

(51) Int. Cl.
*A01N 65/00*     (2006.01)

(52) U.S. Cl. ...................................... 424/724; 514/909

(58) Field of Classification Search .............. 424/725, 424/476, 764, 769; 514/909
See application file for complete search history.

(56) References Cited

U.S. PATENT DOCUMENTS

| | | | |
|---|---|---|---|
| 5,667,793 A | * | 9/1997 | Cho et al. |
| 5,705,170 A |   | 1/1998 | Kong et al. |
| 5,972,340 A | * | 10/1999 | Dos Santos |
| 2002/0197338 A1 |   | 12/2002 | Tseng et al. |

FOREIGN PATENT DOCUMENTS

| | | | |
|---|---|---|---|
| BE | 1 009 545 A6 | | 5/1997 |
| CN | WO 01/64229 A1 | * | 9/2000 |
| CN | 1302646 A | * | 7/2001 |
| DE | 236 446 C | | 7/1911 |
| DE | 277 061 C | | 7/1914 |
| ES | 2 049 661 | | 4/1994 |
| FR | 4 582 M | | 11/1966 |
| FR | 2576212 A | * | 7/1986 |
| FR | 2 716 374 A1 | | 8/1995 |
| GB | 689533 | | 4/1953 |
| JP | 2000063260 A | * | 2/2000 |
| JP | 2000086527 A | * | 3/2000 |
| JP | 2002138045 A | * | 5/2002 |
| SU | 1792701 A1 | * | 2/1993 |
| WO | WO 200004047 A1 | * | 1/2000 |

OTHER PUBLICATIONS http://www.evitamins.com/product.asp?pid=1881, "StiVectin SD™ by Klein-BEcker", downloaded Jan. 9, 2006.*
http://www.strivectin.com/strivectin-story.php, "StriVectin-SD® / (Stridril® ): Scientifica Breakthrough or Dumb Luck?", downloaded Jan. 9, 2006.*
http://www.npd.com/dynamic/releases/press_040719.htm, "NPD reports strong sales of StriVectin-SD, despite low awareness", downloaded on Jan. 9, 2006.*
http://www.nps.gov/plants/alien/fact/imcy1.htm, Cogon grass: Imperata cylindrica (L.) Palisot, Grass family (Poaceae), downloaded Jan. 9, 2006.*
http://www.ibiblio.org/pfaf/cgi-bin/arr_html?Imperata+cylindrica&CAN=COMIND, Plants for a Future: Database Search Results, Imperata cylindrica, downloaded Jan. 9, 2006.*
http://www.ibiblio.org/pfaf/cgi-bin/arr_html?Hemerocallis+plicata&CAN=LATIND, Plants for a Future: Database Search Results, Hemerocallis plicata, downloaded Jan. 9, 2006.*
Derwent Publications, AN 2002-455340, XP-002315397, CN 1339309, Mar. 13, 2002.
Derwent Publications, AN 1999-459166, XP-002315398, CN 1217203, May 26, 1999.
Patent Abstracts of Japan, JP 2000-063227, Feb. 29, 2000.
Patent Abstracts of Japan, JP 2000-063260, Feb. 29, 2000.
Patent Abstracts of Japan, JP 10-158181, Jun. 16, 1998.
Derwent Publications, AN 2000-075216, XP-002315399, JP 2000-086527, Mar. 28, 2000.
Patent Abstracts of Japan, JP 2002-356434, Dec. 13, 2002.

* cited by examiner

*Primary Examiner*—Michele C. Flood
(74) *Attorney, Agent, or Firm*—Oblon, Spivak, McClelland, Maier & Neustadt, P.C.

(57) ABSTRACT

A lipolysis stimulator and a slimming agent which stimulate or facilitate lipolysis of accumulated adipose tissue, to thereby exert the body slimming effect. The lipolysis stimulator or the slimming agent of the present invention contains as an active ingredient any form of a plant or an extract thereof, the plant being selected from among common juniper, togenashi, rosehip, *areca, polygala* root, *plantago* herb, *calumba*, zuikorodoku, garden *nasturtium*, kidachi-umanosuzukusa, bayberry, cogon grass, kohon, shoyokanzo, Japanese white birch, tanjin, kikubafuro, white mustard, common sunflower, ground ivy, Chinese wolfberry, Japanese pagota tree, sennenken, common fig, kankatto, Chinese hibiscus, usubaakaza, fenugreek, English walnut, sozuku, koniwa-zakura, *gardenia*, shima-kan-giku, akamino-akane, futaba-mugura, karoou, schizonepeta spike, purslane, karabyakushi, and prostrate knotweed.

5 Claims, No Drawings

LIPOLYSIS STIMULATOR

FIELD OF THE INVENTION

The present invention relates to a lipolysis stimulator and a slimming agent.

BACKGROUND OF THE INVENTION

Obesity arises as a result of accumulation of neutral fat in white adipocytes, due to excessive energy intake over energy expenditure. As has been pointed out, a type of obesity accompanying significant accumulation of visceral fat has some relation with certain pathological conditions such as insulin resistance and arteriosclerosis, and another type of obesity accompanying significant accumulation of subcutaneous fat has become a concern to both men and women from the aesthetic point of view.

Hitherto, it has been widely accepted that obesity can be well suppressed, prevented, or reversed by habitual drinking of oolong tea or eucommia leaf tea. Moreover, for suppressing calorie intake, a variety of means have been implemented; e.g., limiting meals, consuming low-energy foods, and taking appetite suppressors or digestion/absorption suppressors. However, habitual drinking of oolong tea or eucommia leaf tea, or suppression of calorie intake, is not necessarily sufficient for preventing or reversing obesity. In addition, such means is difficult for people to accept as a habit. Furthermore, these means are not a radical solution, as they do not stimulate lipolysis of accumulated fat.

Incidentally, noradrenaline, adrenaline, and similar hormones in the body have conventionally been known as stimulating lipolysis. For example, compounds such as caffeine and theophylline have been reported to stimulate the lipolysis activity of the hormone (see, for example, Japanese Patent Application Laid-Open (kokai) No. 53-59038). However, long-term administration of such hormones for slimming purposes should be avoided, from the viewpoint of safety.

SUMMARY OF THE INVENTION

The present invention provides a lipolysis stimulator and a slimming agent, containing as an active ingredient any form of a plant or an extract thereof, the plant being selected from among common juniper, togenashi, rosehip, *areca, polygala* root, *plantago* herb, *calumba*, zuikorodoku, garden *nasturtium*, kidachiumanosuzukusa, bayberry, cogon grass, kohon, shoyokanzo, Japanese white birch, tanjin, kikubafuro, white mustard, common sunflower, ground ivy, Chinese wolfberry, Japanese pagota tree, sennenken, common fig, kankatto, Chinese hibiscus, usubaakaza, fenugreek, English walnut, sozuku, koniwa-zakura, *gardenia*, shima-kan-giku, akamino-akane, futaba-mugura, karoou, schizonepeta spike, purslane, karabyakushi, and prostrate knotweed.

The present invention also provides a slimming method including applying the plant or an extract thereof to the skin.

The present invention also provides use of the plant or an extract thereof in manufacture of a lipolysis stimulator or a slimming agent.

DETAILED DESCRIPTION OF THE INVENTION

The present invention contemplates provision of a lipolysis stimulator and a slimming agent which stimulate lipolysis of accumulated adipose tissue, in particular, subcutaneous fat, to thereby exert slimming effect with high safety. The present inventors searched for a natural substance which stimulates lipolysis and is safe to human body, and found that a certain plant (such as common juniper) or its extract stimulates lipolysis of neutral fat accumulated in adipose tissue, and is therefore useful as a drug, food, or a cosmetic composition which is capable of providing a slimming effect through suppression, prevention, or reversal of obesity.

With the lipolysis stimulator or the slimming agent of the present invention, slimming of the body can be realized through suppression, prevention, or reversal of obesity.

In the plants of the present invention, common juniper refers, in its narrow sense, to *Juniperus communis* which belongs to family Cupressaceae. However, analogous plants belonging to family *Juniperus* may also be used in the present invention. Similarly, togenashi refers to *Rosa normalis* belonging to family Rosaceae; rosehip refers to *Rosa canina* belonging to family Rosaceae; areca refers to *Areca catechu* belonging to family Palmae; *polygala* root refers to *Polygala tenuifolia* belonging to family Polygalaceael; *plantago* herb refers to *Plantago asiatica* belonging to family Plantaginaceae; calumba refers to *Jaterorhiza columba* belonging to family Menispermaceae; zuikorodoku refers to *Stellera chamaejasme* L. belonging to family Thymelaeaceae; garden *nasturtium* refers to *Trollius chinensis* Bge. belonging to family Ranunculaceae; kidachiumanosuzukusa refers to *Aristolochia manshuriensis* Kom. belonging to family Aristolochiales; bayberry refers to *Myrica rubra* Sieb. et Zucc. belonging to family Myricaceae; cogon grass refers to *Imperata cylindrica* belonging to family *Imperata cylindrica* (L.) P. Beauvois var. *koenigii* (Retz.) Durand et Schinz. (I. cylindrica), kohon refers to *Ligusticum sinense* Oliv. belonging to family Apiaceae (Umbelliferae); shoyokanzo refers to *Hemerocallis plicata* Stapf belonging to family Liliaceae, Japanese white birch refers to *Betula platyphylla* Suk. Var. *japonica* (Sieb.) Hara belonging to family Betulaceae; tanjin refers to *Salvia miltiorrhiza* Bge. belonging to family Lamiacea (Labiatae); kikubafuro refers to *Erodium stephanianum* Willd. belonging to family Geraniaceae; white mustard refers to *Brassica hirta* Moench (=*B. alba* (L.) Boiss.) belonging to family Brassicaceae (Crusiferae); common sunflower refers to *Helianthus annuus* L. belonging to family Asteraceae; ground ivy refers to *Glechoma hederacea* L. var. *grandis* (A. Gary) Kudo (*Glechoma hederacea* L.) belonging to family Lamiaceae; Chinese wolfberry refers to *Lycium chinense* Mill., *L. barbarum* L. belonging to family Solanaceae; Japabese pagota tree refers to *Sophora japonica* L. belonging to family Fabaceae (Leguminosae); sennenken refers to *Homalomena occulta* (Lour.) Schott belonging to family Araceae; common fig refers to *Ficus carica* L. belonging to family Moraceae; kankatto refers to *Pueraria thomsonii* Benth. belonging to family Fabaceae (Leguminosae); Chinese hibiscus refers to *Hibiscus rosa-sinensis* L. belonging to family Malvaceae; usubaakaza refers to *Chenopodium hybridum* L. belonging to family Chenopodiaceae; fenugreek refers to *Trigonella foenumgraecum* L. belonging to family Fabaceae (Leguminosae); English walnut refers to *Juglans regia* L. belonging to family Juglandaceae; sozuku refers to *Alpinia katsumadai* Hayata belonging to family Zingiberaceae; koniwa-zakura refers to *Prunus humilis* Bge. *P. japonica* Thunb., *P. tomentosa* thunb. belonging to family Rosaceae; *gardenia* refers to *Gardenia jasminoides* Ellis, *G. jasminoides* Ellis var. *grandiflora* Nakai belonging to family Chenopodiaceae; shima-kan-giku refers to *Chrysanthemum indcum* L. belonging to family Asteraceae; akamino-akane refers to *Rubia cordifolia* L. belonging to family Chenopodiaceae; futaba-mugura refers to *Hedyotis diffusa* Willd. (=*Oldenlandia diffusa* (Willd.) Roxb. belonging to family Chenopodiaceae; karoou refers to *Lysimachia christinae* Hance belonging to family Primulaceae; schizonepeta spike refers to *Schizonepeta tenuifolia* Briq. belonging to family Lamiaceae (Labiatae); purslane refers to *Portulaca oleracea* L. belonging to family purslane (*Portulaca oleracea*); karabyakushi refers to *Angelica dahurica* Benth. et Hook. var. pai-chi Kimura, Hata et Yen belonging to family Apiaceae (Umbelliferae); and prostrate knotweed refers to *Polygonum aviculare* L. belonging to family Polygonaceae. Analogous plants belonging to the genera of the above-listed plants may also be employed for the purposes of the present invention.

In the present invention, any part of the above-listed plants may be employed as appropriate. For example, the whole plant, leaves, bark, branches, fruits, or roots may be used in their original forms or after processing (milled or pulverized). Preferred portions of plants are as follows: fruit of common juniper; fruit of togenashi; fruit of rosehip; the whole plant of *plantago* herb; seeds of *areca*; roots of *polygala* root; roots of *calumba*; roots of zuikorodoku; flowers of garden *nasturtium*; stems of kidachiumanosuzukusa; barks of bayberry; rhizomes of cogon grass; rhizomes of kohon; flowers of shoyokanzo; barks of Japanese white birch; roots of tanjin; the whole plant of kikubafuro; seeds of white mustard; seeds of common sunflower; the whole plant of ground ivy; fruit of Vhinese wolfberry; flowers of Japanese pagota tree; rhizomes of sennenken; fruit of common fig; roots of kankatto; flowers of Chinese hibiscus; the whole plant of usubaakaza; seeds of fenugreek; seeds of English walnut; seeds of sozuku; seeds of koniwazakura; fruit of *gardenia*; flowers of shima-kan-giku; roots of akamino-akane; the whole plant of futaba-mugura; the whole plant of karoou; the whole plant of schizonepeta spike; the whole plant of purslane; roots of karabyakushi; and the whole plant of prostrate knotweed.

In the context of the present invention, the word "extract" of any of the above-mentioned plants refers to an extract obtained by subjecting any part of the plant to an extraction procedure at ambient temperature or under heat with an appropriate solvent without use of any special extraction device or through use of a specific extractor such as a Soxhlet's extractor; a diluted solution of an extract; a concentrate of an extract; or a dry powder of an extract.

The extraction solvent to be used for obtaining the plant extract of the present invention may be either polar or non-polar solvent. A mixture of a polar and a non-polar solvent may also be employed. Examples of the solvent include water; alcohols such as methanol, ethanol, propanol, and butanol; polyhydric alcohols such as propylene glycol and butylene glycol; ketones such as acetone and methyl ethyl ketone; esters such as methyl acetate and ethyl acetate; linear or cyclic ethers such as tetrahydrofuran and diethyl ether; polyethers such as polyethylene glycol; hydrocarbons such as hexane, cyclohexane, and petroleum ether; aromatic hydrocarbons such as benzene and toluene; pyridines; super critical carbon dioxide; fats and oils; waxes; and other types of oils. Of these materials, water, alcohols, and water-alcohol mixtures are preferred, with water-ethanol mixtures, inter alia, a water-ethanol mixture which contains 20 to 80% (vol/vol) ethanol being particularly preferred.

Extraction conditions may differ depending on the solvent employed. When the solvent is water, ethanol, or a water-ethanol mixture, preferably, 1 to 100 parts by weight of solvent is used for 1 part by weight of plant, and extraction is carried out at 5 to 70° C., preferably 10 to 60° C., for 1 hour to 30 days, preferably for 7 days to 14 days.

The resultant extract may be used as is, but may also be used after being processed. For example, the extract may be diluted, concentrated, or freeze-dried. Optionally, they may further be processed into a powder or a paste.

Alternatively, the extract may be used after subjecting to a liquid-liquid partition or a similar technique, to thereby remove inert contaminants. In the context of the present invention, use of an extract which has undergone such a process is preferred. If desired, the thus-obtained contaminant-free extract may be further subjected to a conventionally known deodorizing or decoloring procedure before use.

In the present invention, a plant or an extract thereof may be used as a mixture of two or more species.

As described hereinbelow in the Examples section, in rat abdominal subcutaneous adipose tissue, a plant or an extract thereof according to the present invention synergistically potentiates the lipolysis activity of norepinephrine. Therefore, through administration of such a plant or extract to a subject of interest, the body of the subject can be slimmed. Moreover, since the above activity is also exerted in the visceral adipose tissue, a composition which contains an effective amount of the plant or plant extract can serve as a lipolysis stimulator or a slimming agent which exerts suppressing, preventive or reversal effect against obesity; or in other words, the slimming effect. In short, the lipolysis stimulator and the slimming agent of the present invention stimulate lipolysis of neutral fat stored in adipose tissue, in particular, subcutaneous fat, to thereby exhibit suppressing, preventive or reversal effect against obesity; or in other words, the slimming effect. Therefore, the lipolysis stimulator and the slimming agent of the present invention can be used as a cosmetic product, a quasi-drug, a drug, or a food, for body slimming purposes.

Although the amount of the active ingredient of the lipolysis stimulator or the slimming agent may differ depending on, for example, the form of that ingredient and the manner of administration, it may be selected from broad ranges. For example, in the case where a product of external use is the target product, the active ingredient is incorporated therein in an amount of 0.005 wt. % or more, preferably 0.01 to 30 wt. %, more preferably 0.2 to 25 wt. %, even more preferably 2 to 20 wt. % (all calculated on a dry basis after extracted with a solvent), with respect to the entirety of the composition, whereas in the case where an orally administered product is the target product, the product preferably contains, in a daily dose for an adult, the active ingredient in an amount of 0.01 to 10 g, preferably 0.1 to 5 g, more preferably 1.0 to 5 g (all calculated on a dry basis after extracted with a solvent).

The lipolysis stimulator or the slimming agent of the present invention may optionally contain, according to needs, any suitable combinations of various additives which are used in cosmetics, quasi-drugs, drugs, foods, or the like fields; or various pharmaceutically active ingredients. Examples of the additives include powders such as chalk, talc, fuller's earth, kaolin, starch, rubber, and colloidal silica sodium polyacrylate; oils or oily substances such as mineral oil, vegetable oil, and silicone oil; emulsifiers such as sorbitan trioleate, sorbitan tristearate, glycerol monooleate, and silicone polymer surfactants; preservatives such as p-hydroxybenzoate ester; antioxidants such as butyl hydroxytoluene; wetting agents such as glycerol, sorbitol, 2-pyrrolidone-5-carboxylate, dibutylphthalate, gelatin, and polyethylene glycol; buffers such as lactic acid-base (triethanolamine or sodium hydroxide); surfactants such as glycerol ether, and synthesized, animal, or vegetable ceramides; waxes such as beeswax, ozokerite wax, and paraffin wax; thickening agents; activators; colorants; and perfumes. Examples of the pharmaceutically active ingredients include UV absorbers, anti-inflammatory agents, germicides, antioxidants, vitamins, and pharmaceuticals or natural products with fat metabolism promoting effect or uncoupling protein expression promoting effect (e.g. xanthine derivatives, β-adrenergic stimulants, α-adrenergic inhibitors, bipyridine derivatives, isoflavonic acid, rosisterol, octacosanol, hydoxytyrosol, grapefruit oil, raspberry ketone, zingerone, thistle (*Cirsium*), family Piperaceae, family Rutaceae, family Menispermaceae, *Kigelia* plants, *Gynostemma pentaphyllum*, Atractylodis lanceae Rhizoma, benzoin (*Styrax benzoin*), *Coix lacryma-jobi*, azuki bean (*Vigna angularis* (Willd)), fennel (*Foeniculum vulgare*), Tabebuia, *Geranium thunbergii*, *Scutellaria baicalensis*, peach, garden thyme (*Thymus vulgaris*), Chinese peony (*Paeonia lactiflora*), tea leaves, *Cola acuminata*, *Swertia Japonica*, Cinnamomi Cortex, *Sanguisorba officinalis*, sage (*Salvia officinalis*), loquat (*Eriobotrya Japonica* (Thunb.) Lindl.), bladderwrack (*fucus evanescens*), carrot, shiitake mashroom, beefsteak geranium (*Saxifraga stolonifera*), ginkgo (*Ginkgo Biloba*), and other vegetable extracts).

The lipolysis stimulator and the slimming agent of the present invention may be formulated into external-use products, or alternatively, into internal products, injection products, or any other product forms. Example forms include tablets, capsules, liquids, powders, granules, creams, milky lotions, jells, pastes, cataplasms, plasters, sticks, sheets, and tea bags, and they may be appropriately used for oral administration or for the preparation of foods, external medicines, bath-additives, or body detergents, or may be used during taking a shower.

The slimming method according to the present invention is characterized by applying to the body the plant or an extract thereof of the present invention. In the context of the present invention, the expression "slimming method" means an esthetic method performed for achieving a slender body with a favorable look.

EXAMPLES

The present invention will next be described in more detail by way of examples.

Production Example 1

Production of a Common Juniper Extract

A common juniper extract W (1 mL; product of Maruzen Pharmaceuticals Co., Ltd.), which is an extract of the fruit of common juniper with water as a solvent, was thermally processed at 105° C. for 8 hours, whereby a dry matter of the extract (21 mg) was obtained (Invention product 1).

Production Example 2

Production of a Togenashi Extract

A togenashi extract G (1 mL; product of Maruzen Pharmaceuticals Co., Ltd.), which is an extract of the fruit of togenashi with 50% aqueous 1,3-butylene glycol solution as a solvent, was thermally processed at 105° C. for 8 hours, whereby a dry matter of the extract (9 mg) was obtained (Invention product 2).

Production Example 3

Production of a Rosehip Extract

A Pharcolex *Rosa canina* E (1 mL; product of Ichimaru Pharcos Co., Ltd.), which is an extract of the fruit of *Rosa canina* with 50% aqueous ethanol solution as a solvent, was thermally processed at 105° C. for 8 hours, whereby a dry matter of the extract (25 mg) was obtained (Invention product 3).

Production Example 4

Production of an *areca* Extract

An extract (1 mL) obtained by extracting seeds of *areca* (10 g) with 50% aqueous ethanol solution as a solvent was thermally processed at 105° C. for 8 hours, whereby a dry matter of the extract (26 mg) was obtained (Invention product 4).

Production Example 5

Production of a *polygala* Root Extract

An extract (1 mL) obtained by extracting roots of *polygala* root (10 g) with 50% aqueous ethanol solution as a solvent was thermally processed at 105° C. for 8 hours, whereby a dry matter of the extract (126 mg) was obtained (Invention product 5).

Production Example 6

Production of a *plantago* Herb Extract

An extract (1 mL) obtained by extracting the whole plant of *plantago* herb (5 g) with 50% aqueous ethanol solution as a solvent was thermally processed at 105° C. for 8 hours, whereby a dry matter of the extract (34 mg) was obtained (Invention product 6).

Production Example 7

Production of a Calumba Extract

An extract (1 mL) obtained by extracting roots of calumba (10 g) with 50% aqueous ethanol solution as a solvent was thermally processed at 105° C. for 8 hours, whereby a dry matter of the extract (54 mg) was obtained (Invention product 7).

Production Example 8

Production of a Zuikorodoku Extract

To one g of roots of zuikorodoku, 10 mL of 50% aqueous ethanol solution was added, followed by an extraction step at room temperature for 7 days. The resultant extract was found to contain an extract of Invention product 8, which is obtained through thermal treatment at 105° C. for 8 hours, in an amount of 1.24 w/v %.

Through a similar procedure, respective extracts as shown in Table 1 (Invention products 9 to 42 and Comparative products 1 to 3) were obtained. In Table 1, "hot water" means that extraction was performed with hot water for one hour.

TABLE 1

| Sample | Plant | Extraction solvent | Evaporation residue (w/v %) |
|---|---|---|---|
| Example product 9 | garden nasturtium | 50% aqueous ethanol | 3.25 |
| Example product 10 | kidachiumano-suzukusa | 50% aqueous ethanol | 1.50 |
| Example product 11 | bayberry | 50% aqueous ethanol | 1.80 |
| Example product 12 | cogon grass | 50% aqueous ethanol | 2.74 |
| Example product 13 | kohon | 50% aqueous ethanol | 2.07 |
| Example product 14 | shoyokanzo | 50% aqueous ethanol | 5.36 |
| Example product 15 | Japanese white birch | 50% aqueous ethanol | 1.45 |
| Example product 16 | tanjin | 50% aqueous ethanol | 4.71 |
| Example product 17 | kikubafuro | 50% aqueous ethanol | 1.46 |
| Example product 18 | white mustard | 50% aqueous ethanol | 1.47 |
| Example product 19 | common sunflower | 50% aqueous ethanol | 0.82 |
| Example product 20 | ground ivy | 50% aqueous ethanol | 3.60 |
| Example product 21 | Chinese wolfberry | 50% aqueous ethanol | 6.05 |
| Example product 22 | Japanese pagota tree | 50% aqueous ethanol | 3.61 |
| Example product 23 | sennenken | 50% aqueous ethanol | 1.55 |
| Example product 24 | common fig | 50% aqueous ethanol | 3.05 |
| Example product 25 | kankatto | 50% aqueous ethanol | 1.34 |
| Example product 26 | Chinese hibiscus | 50% aqueous ethanol | 2.97 |
| Example product 27 | usubaakaza | 50% aqueous ethanol | 1.73 |
| Example product 28 | fenugreek | 50% aqueous ethanol | 1.40 |
| Example product 29 | English walnut | 50% aqueous ethanol | 0.72 |
| Example product 30 | sozuku | 50% aqueous ethanol | 0.91 |
| Example product 31 | koniwa-zakura | 50% aqueous ethanol | 0.96 |
| Example product 32 | gardenia | 50% aqueous ethanol | 1.91 |
| Example product 33 | shima-kan-giku | 50% aqueous ethanol | 2.93 |
| Example product 34 | akamino-akane | 50% aqueous ethanol | 1.50 |
| Example product 35 | futaba-mugura | 50% aqueous ethanol | 1.44 |
| Example product 36 | karoou | 50% aqueous ethanol | 1.13 |
| Example product 37 | schizonepeta | 50% aqueous ethanol | 1.02 |
| Example product 38 | purslane | 50% aqueous ethanol | 2.16 |
| Example product 39 | karabyakushi | 50% aqueous ethanol | 1.53 |
| Example product 40 | prostrate knotweed | 50% aqueous ethanol | 1.50 |
| Example product 41 | cogon grass | hot water | 2.98 |
| Example product 42 | cogon grass | ethanol | 1.88 |
| Comparative product 1 | oolong tea | hot water | 12.8 |
| Comparative product 2 | oolong tea | 30% aqueous ethanol | 11.9 |
| Comparative product 3 | Eucommia leaf tea | hot water | 13.1 |

Example 1

The above-described Example products 1 to 42 and Comparative products 1 to 3 were tested as described below for their lipolysis stimulating activity. The resulta are shown in Table 2 (Tables 2-1 and 2-2).

[Test Method]

The Rodbell's method was used (Rodbell, M., J. Biol. Chem., 239, 375 (1964)). Specifically, from the abdominal subcutaneous adipose tissue of each of one to three male Wistar rats (each weighing 150 to 200 g), isolated adipocytes were prepared by use of a collagenase solution. The test material was a dried extract or an extract (liquid form). The prepared cells were incubated at 37° C. for 2 hours in a Hanks buffer solution containing bovine serum albumin to which the test material and norepinephrine were added at a concentration of 10 μg/mL on a dry matter basis and 0.3 μM, respectively. The resultant free glycerol was assayed by the enzyme method. As a control, incubation was carried out in the presence of norepinephrine alone (without the test material). Lipolysis stimulation activity was calculated by the following equation. The results obtained from a double run of test are shown.

Lipolysis stimulation activity (%)=(Released glycerol value in each group)÷(Released glycerol value in control group)×100

TABLE 2-1

| Sample | Lipolysis stimulation activity (%)[1] |
|---|---|
| Control | 100 |
| Example product 1 | 221 |
| Example product 2 | 221 |
| Example product 3 | 199 |
| Example product 4 | 186 |
| Example product 5 | 159 |
| Example product 6 | 157 |
| Example product 7 | 150 |
| Example product 8 | 283 |
| Example product 9 | 268 |
| Example product 10 | 341 |
| Example product 11 | 215 |
| Example product 12 | 2278 |
| Example product 13 | 2057 |
| Example product 14 | 3081 |
| Example product 15 | 198 |
| Example product 16 | 192 |
| Example product 17 | 228 |
| Example product 18 | 275 |
| Example product 19 | 256 |
| Example product 20 | 233 |

[1] unit = %, The same test was repeated 2-4 times. In the Table, average values are shown (n = 2 to 3).

TABLE 2-2

| Sample | Lipolysis stimulation activity (%)[1] |
|---|---|
| Example product 21 | 326 |
| Example product 22 | 238 |
| Example product 23 | 269 |
| Example product 24 | 335 |
| Example product 25 | 256 |
| Example product 26 | 267 |
| Example product 27 | 259 |
| Example product 28 | 669 |
| Example product 29 | 1577 |
| Example product 30 | 1363 |

TABLE 2-2-continued

| Sample | Lipolysis stimulation activity (%)[1] |
|---|---|
| Example product 31 | 1835 |
| Example product 32 | 1166 |
| Example product 33 | 1424 |
| Example product 34 | 659 |
| Example product 35 | 793 |
| Example product 36 | 431 |
| Example product 37 | 1271 |
| Example product 38 | 720 |
| Example product 39 | 1768 |
| Example product 40 | 1165 |
| Example product 41 | 1516 |
| Example product 42 | 1887 |
| Comparative product 1 | 105 |
| Comparative product 2 | 98 |
| Comparative product 3 | 104 |

[1]unit = %, The same test was repeated 2-4 times. In the Table, average values are shown (n = 2 to 3).

As is apparent from Table 2, when 10 µg/mL of a test material is applied to dissociated adipocytes, clear lipolysis stimulating effect was observed in relation to Example products 1 to 42, whereas when any of Comparative products 1 to 3 was used, no such effect was obtained. Therefore, it has been substantiated that the Example products exhibit lipolysis stimulating effect on adipocytes.

The invention claimed is:

1. A slimming method comprising applying an effective amount of a lipolysis stimulator comprising as an active ingredient an aqueous or aqueous ethanol plant extract, of *shoyokanzo* (*Hemerocallis plicata* Stapf belonging to family Liliaceae), to the skin of a subject.

2. The slimming method of claim 1, wherein said lipolysis stimulator comprises as an active ingredient 0.005 weight (wt.) % or more, calculated on a dry basis of said aqueous or aqueous ethanol plant extract based on the entirety of said composition.

3. The slimming method of claim 1, wherein said lipolysis stimulator comprises as an active ingredient 0.01 to 30 wt. %, calculated on a dry basis of said aqueous or aqueous ethanol plant extract based on the entirety of said composition.

4. The slimming method of claim 1, wherein said lipolysis stimulator comprises as an active ingredient 0.02 to 25 wt. %, calculated on a dry basis of said aqueous or aqueous ethanol plant extract based on the entirety of said composition.

5. The slimming method of claim 1, wherein said lipolysis stimulator comprises as an active ingredient 2 to 20 wt. %, calculated on a dry basis of said aqueous or aqueous ethanol plant extract based on the entirety of said composition.

* * * * *